United States Patent
Kreindel

(10) Patent No.: US 6,939,344 B2
(45) Date of Patent: Sep. 6, 2005

(54) METHOD FOR CONTROLLING SKIN TEMPERATURE DURING THERMAL TREATMENT

(75) Inventor: Michael Kreindel, Haifa (IL)

(73) Assignee: Syneron Medical Ltd., Haifa (IL)

( * ) Notice: Subject to any disclaimer, the term of this patent is extended or adjusted under 35 U.S.C. 154(b) by 0 days.

(21) Appl. No.: 09/920,295

(22) Filed: Aug. 2, 2001

(65) Prior Publication Data

US 2003/0028186 A1 Feb. 6, 2003

(51) Int. Cl.[7] .............................................. A61B 18/18

(52) U.S. Cl. ........................ 606/9; 606/10; 606/11; 606/32; 606/35; 607/96; 607/101; 607/102

(58) Field of Search .......................... 606/8–12, 32–35, 606/38, 41, 42; 607/88–92, 96–102

(56) References Cited

U.S. PATENT DOCUMENTS

| | | | | |
|---|---|---|---|---|
| 4,057,063 A | * | 11/1977 | Gieles et al. | 128/303.17 |
| 4,679,561 A | * | 7/1987 | Doss | 128/422 |
| 5,190,517 A | * | 3/1993 | Zieve et al. | 604/22 |
| 5,643,257 A | | 7/1997 | Cohen et al. | |
| 6,053,909 A | * | 4/2000 | Shadduck | 606/3 |
| 6,391,026 B1 | * | 5/2002 | Hung et al. | 606/41 |
| 6,402,742 B1 | * | 6/2002 | Blewett et al. | 606/34 |

\* cited by examiner

Primary Examiner—A. Farah
(74) Attorney, Agent, or Firm—Browdy and Neimark, P.L.L.C.

(57) ABSTRACT

A system and method for treating skin. The system comprises a source of radiation for irradiating the skin and a pair of electrodes for applying a voltage to the skin. An electrical meter measures an electrical response of the skin to the applied voltage. A processor adjusts a parameter of the radiation based upon the measured response. The invention may be used to control skin temperature during thermal treatment.

16 Claims, 2 Drawing Sheets

METHOD FOR CONTROLLING SKIN TEMPERATURE DURING THERMAL TREATMENT

FIELD OF THE INVENTION

This invention relates to medical devices, and more specifically for such devices for use in, dermatology.

BACKGROUND OF THE INVENTION

There are many medical and cosmetic treatments that utilize electro-magnetic radiation to destroy a local defect in skin. Among these are laser-assisted hair removal, vascular lesion treatment and skin rejuvenation. In these treatments, the defect is irradiated, and heat formed in the skin in and near the defect, destroys the defect. The main problem limiting broad use of these treatments is the risk of thermal damage to skin surrounding the defect. One way to reduce this risk is to monitor skin temperature during the irradiation, and to stop the irradiation before the skin becomes overheated. However, surface skin temperature measurements give information relating only to the superficial skin layer, composed of dead cells (stratum corneum), while the temperature of the underlying living tissue can differ significantly.

One method for assessing tissue temperature relies on measurement of the electrical impedance of the tissue, which is temperature dependent. Tissue impedance decreases 1% to 3% for every centigrade degree increase in. temperature (Francis A. Duck, Physical properties of tissue, a Comprehensive Reference Book, Academic Press, 1990, p. 173), U.S. Pat. No. 5,643,257, discloses a method for invasive thermal treatment of varicose veins, in which irradiation intensity is reduced when the tissue impedance drops below a predetermined value.

SUMMARY OF THE INVENTION

The present invention provides a device and method for irradiating skin. In accordance with the invention a skin defect is irradiated with electro-magnetic radiation. During the irradiation, measurements of an electrical parameter of the skin surrounding die defect are continuously obtained. The electrical parameter is preferably skin impedance, or a parameter known to be correlated with impedance such as conductivity, current and voltage. As the impedance decreases, the intensity of the irradiation is decreased in order to prevent the temperature of the skin surrounding the defect to rise to a level that is detrimental to the skin.

The invention thus provides a system for treating skin, comprising:

(a) a source of radiation configured to irradiate a region of the skin;

(b) at least a first pair of a first electrode and a second electrode, the first and second electrodes being configured to apply a voltage to the skin;

(c) an electrical meter configured to measure an electrical response of the skin to a voltage applied across the electrodes;

(d) a processor configured to adjust a value of a parameter of the radiation based upon a measured electrical response to a voltage applied across the first and second electrodes.

The invention further provides a method for treating skin, comprising:

(a) a source of radiation configured to irradiate a region of the skin;

(b) at least a first pair of a first electrode and a second electrode, the first and second electrodes being configured to apply a voltage to the skin;

(c) an electrical meter configured to measure an electrical response of the skin to a voltage applied across the electrodes;

(d) a processor configured to adjust a value of a parameter of the radiation based upon, a measured electrical response to a voltage applied across the first and second electrodes.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
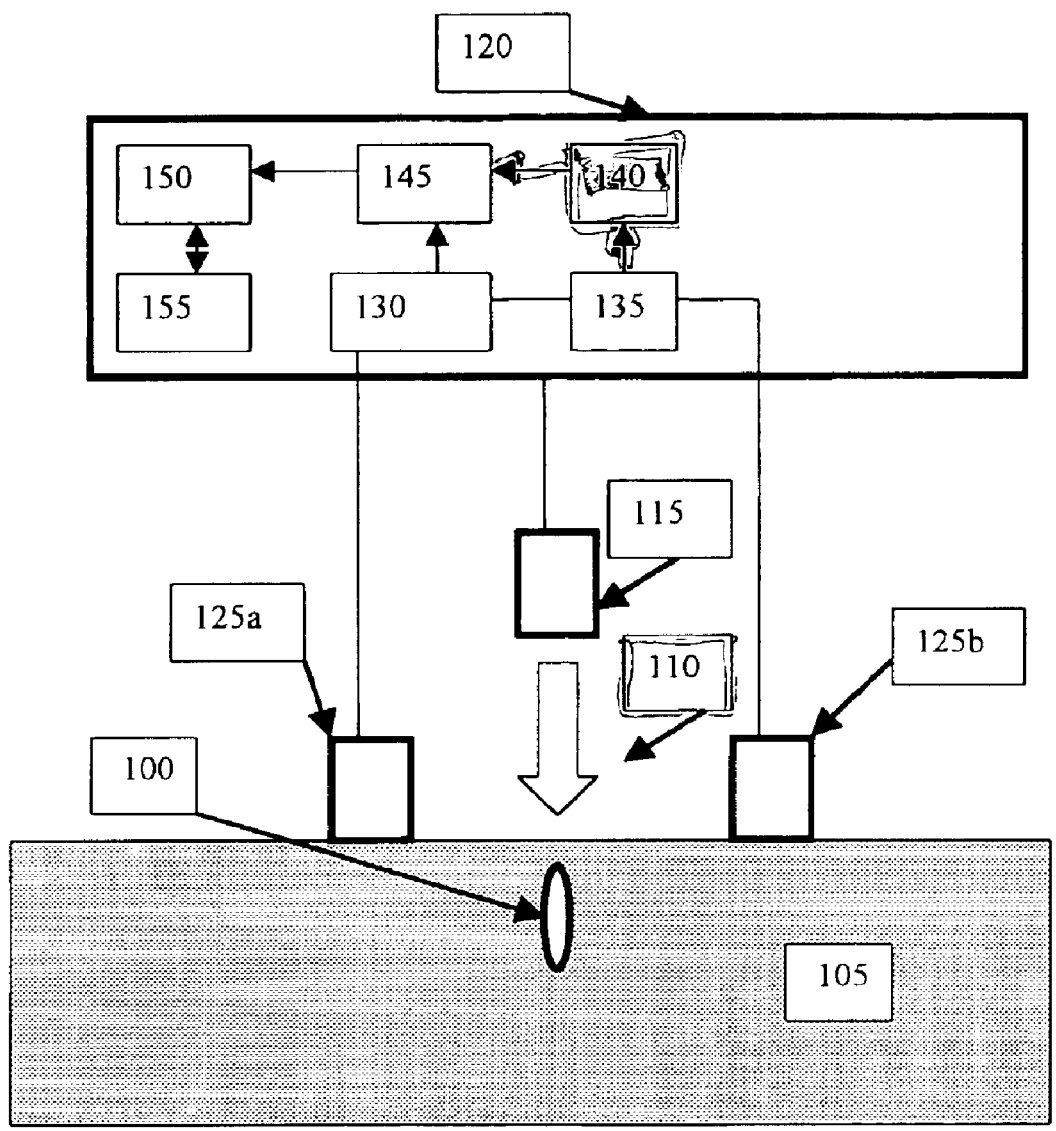
FIG. 1 shows a system for treating skin in accordance with one embodiment of the invention.

Referring first to FIG. 1, a system is shown for treating skin in accordance with one method of the invention. A defect 100 in skin 105 is irradiated with electro-magnetic radiation 110 produced b a source 115. The irradiation 110 has an intensity determined by a controller 120. The controller 120 contains a voltage source 130 that applies an alternating voltage across a first electrode 125a and second electrode 125b. The second electrode 125b may be a grounded electrode that is not connected to the controller 120. An ammeter 135, also located in the controller 120, continuously measures a current flowing between the electrodes 125a and b. An analog output 140 of the ammeter 135 is sampled by an analog to digital converter 145, and the sample values are input to a processor 150.

The processor 150 is configured to determine an electrical response of the slain 105 between the electrodes 125a and b based upon a current measurement made by the ammeter 135. The electrical response may, for example, be skin impedance or conductivity. The processor is further configured to determine a value of one or more parameters to determine the irradiation 110 based upon the electrical response of the skin. 105. The parameter may be, for example, intensity, pulse duration or pulse frequency. The processor 150 then adjusts the parameter of the radiation 110 to the determined value. For example, the processor may store in a memory 155 a table that assigns one or more parameter values to each of one or more non-overlapping impedance ranges. In this example, the processor 150 searches in the table to determine to which impedance range the present impedance measurement belongs. The value of the parameter is then adjusted to the determined value. Typically, the values of the intensities, duration and frequency assigned by the table decrease as the impedance decreases which occurs as the skin temperature rises. In this way, overheating of the skin 105, including its deeper layers, is avoided. As another example, the processor 150 may compare the present impedance measurement to a predetermined threshold value stored in the memory 155. If the impedance measurement is above the predetermined threshold, the intensity, duration or frequency of the irradiation 110 is adjusted to a predetermined value. If the impedance is below the threshold, the irradiation 110 is turned off.

Figure 2:
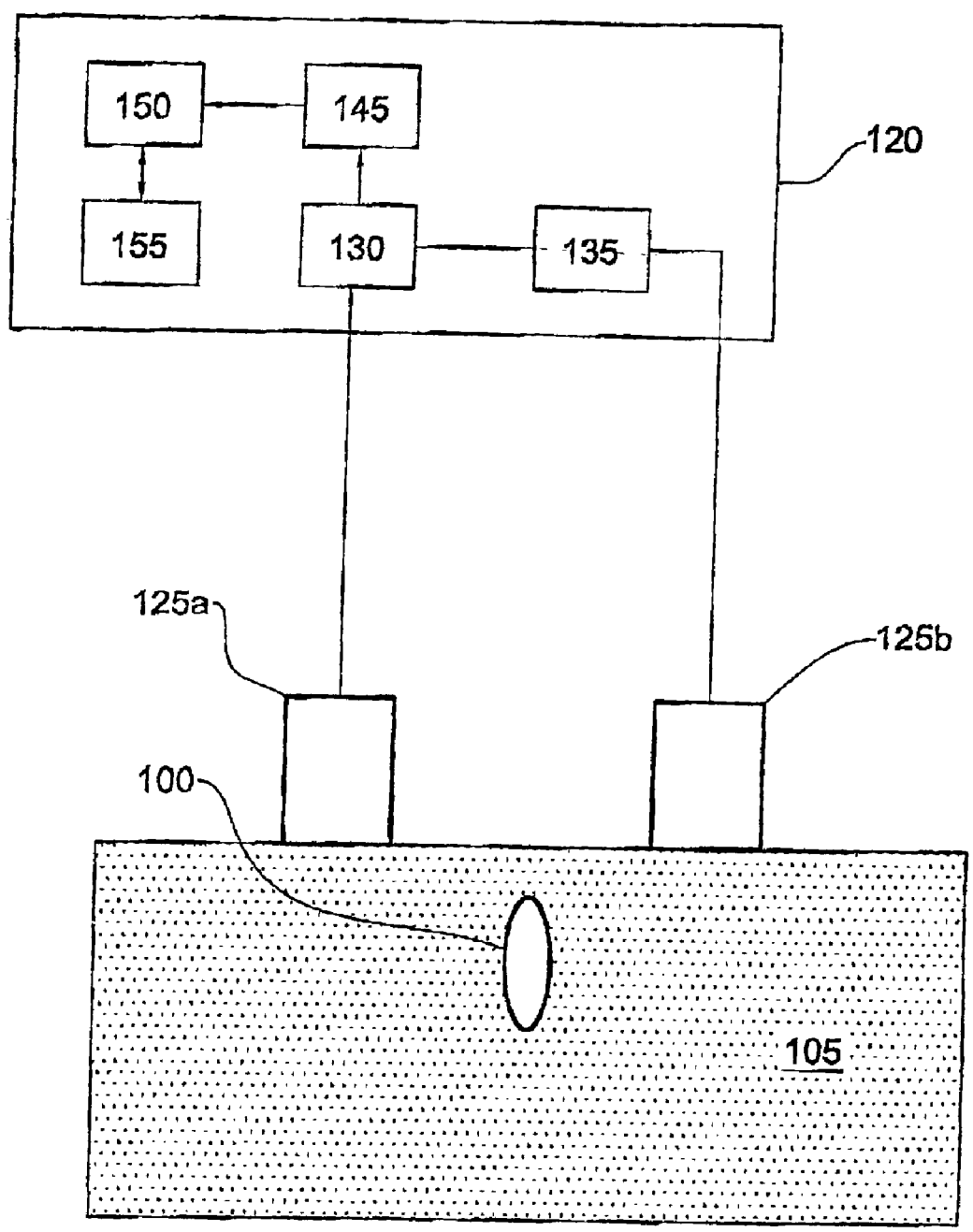
FIG. 2 shows a system for treating skin in accordance with another embodiment of the invention.

Referring now to FIG. 2, a system is shown for treating skin in accordance with another method of the invention. The system shown in FIG. 2 has components in common with the embodiment of FIG. 1, and similar components have the same numerical label in both figures. In this embodiment, a voltage applied across die electrodes 125a and b by the controller 120 is used to measure the skin impedance as in the previous embodiment. In this embodiment, the voltage applied across the electrodes 125a and b is also used to heat the defect 100.

The processor 150 is configured to determine an electrical response of the skin 105 between the electrodes 125a and b based upon a current measurement made by the ammeter 135. The electrical response may be, for example, skin impedance or conductivity. The processor is add configured to determine a voltage based upon the electrical response of the skin 105. The processor 150 then applies the determined voltage across the electrodes 125a and b. For example, the processor may store in a memory 155 a table that assigns a voltage to each of one or more non-overlapping impedance ranges. In this example, the processor 150 searches in the table to determine to which impedance range the present impedance measurement belongs. The voltage assigned to this range is then applied across the electrodes 125a and b. Typically, the voltages assigned by the table decrease as the impedance decreases. In this way, overheating of the skin 105, including its deeper layers, is avoided. As another example, the processor 150 may compare the present impedance measurement to a predetermined threshold value stored in the memory 155. If the impedance measurement is above the predetermined threshold, a predetermined voltage is applied across the electrodes 125a and b. If the impedance is below the threshold, no voltage is applied across the electrodes 125a and b.

What is claimed is:

1. A system for treating skin, comprising:
   (a) a surface radiation assembly configured to irradiate a region on the surface of the skin with electromagnetic radiation;
   (b) a surface electrode assembly structurally separate from said surface radiation assembly and comprising at least a first pair of a first electrode and a second electrode, the first and second electrodes being configured to be applied to the surface of the skin and to apply a voltage to the skin surface;
   (c) an electrical meter configured to measure an electrical response of the skin to a voltage applied across the electrodes; and
   (d) a processor configured to adjust a value of a parameter of the electromagnetic radiation based upon a measured electrical response to a voltage applied across the first and second electrodes.

2. The system according to claim 1, wherein the value of the parameter is adjusted in order to control skin temperature.

3. The system according to claim 1, wherein the parameter is selected from the group comprising:
   1. irradiation intensity;
   2. irradiation pulse duration
   3. irradiation pulse frequency.

4. The system of claim 1 wherein the voltage applied to the skin is in the radio frequency.

5. The system according to claim 1 wherein the electrical response of the skin is skin impedance or a skin conductivity.

6. The system according to claim 5 wherein at least one of the intensity, pulse duration, and pulse frequency of the radiation is decreased by the processor when the skin impedance decreases below a predetermined value.

7. A system for treating skin, comprising:
   (a) a source of radiation configured to irradiate a region of the skin;
   (b) at least a first pair of a first electrode and a second electrode, the first and second electrodes being configured to apply a voltage to the skin;
   (c) an electrical meter configured to measure an electrical response of the skin to a voltage applied across the electrodes, wherein the electrical response of the skin is skin impedance or skin conductivity; and
   (d) a processor configured to adjust value of a parameter of the radiation based upon a measured electrical response to a voltage applied across the first and second electrodes, wherein the processor is further configured to store in a memory a table assigning value of one or more parameters of the irradiation to each of one or more non-overlapping impedance ranges, and the value of a parameter of the radiation is adjusted to a value assigned by the table to an impedance measurement.

8. A method for treating skin comprising:
   (a) irradiating a region of the skin with electromagnetic radiation from a surface radiation assembly;
   (b) applying a voltage to the skin from a surface electrode assembly spaced from the surface radiation assembly;
   (c) measuring an electrical response of the skin to the applied voltage; and
   (d) adjusting a value of a parameter of the electromagnetic radiation from the surface radiation assembly based upon the measured electrical response.

9. The method according to claim 8, wherein the value of the parameter is adjusted in order to control skin temperature.

10. The method according to claim 8 wherein the source of radiation is a voltage applied to the skin.

11. The method of claim 10 wherein the voltage applied to the skin is in the radio frequency range.

12. The method according to claim 8, wherein the parameter is selected from the group comprising:
   1. irradiation intensity;
   2. irradiation pulse duration
   3. irradiation pulse frequency.

13. The method according to claim 8 wherein the electrical response of the skin is a skin impedance.

14. The method according to claim 13 wherein said step of adjusting is performed by a processor, and the at least one of the intensity, pulse duration, and pulse frequency of the radiation is decreased by the processor when the skin impedance decreases below a predetermined value.

15. The method according to claim 13 wherein said step of adjusting is performed by a processor, and the processor is further configured to store in a memory a table assigning value of one or more parameters of the irradiation to each of one or more non-overlapping impedance ranges, and the value of a parameter of the radiation is adjusted to a value assigned by the table to an impedance measurement.

16. The method according to claim 13 wherein said step of adjusting is performed by a processor, and the processor is further configured to store in a memory a threshold, and the value of a parameter of the radiation is adjusted to a predetermined value if the impedance is above a predetermined threshold, and is adjusted to 0 if the impedance is below the threshold.

* * * * *